United States Patent [19]

Weinberger

[11] Plant 4,894

[45] Oct. 12, 1982

[54] NECTARINE TREE

[75] Inventor: John H. Weinberger, Fresno, Calif.

[73] Assignee: Superior Farming Company, Bakersfield, Calif.

[21] Appl. No.: 232,725

[22] Filed: Feb. 9, 1981

[51] Int. Cl.[3] ..... A01H 5/03

[52] U.S. Cl. ..... Plt./41

[58] Field of Search ..... Plt./41

*Primary Examiner*—Robert E. Bagwill

*Attorney, Agent, or Firm*—Roger B. Webster

[57] ABSTRACT

A nectarine tree which is medium in size and vigor, upright-spreading, dense, and round-topped; foliated with medium size, ovate, lanceolate, acutely pointed leaves having a crenate margin, and opposite-irregular, medium size, green, uniform glands; flowers from plump, appressed, pubescent buds of medium size and length; the flowers, of medium season, being large and pink; and is a regular and productive bearer of large, firm-fleshed, visually attractive, globose, freestone fruit, uniform in size and shape, having yellow skin substantially overspread and blushed with red, and yellow flesh.

1 Drawing Figure

BACKGROUND OF THE VARIETY

1. Field of the Invention

In the conduct of an extensive plant breeding program — on behalf of a commercial farming company, and in such company's experimental orchard located near Fresno, Fresno County, Calif. — I have originated a substantial number of new and distinct varieties of fruit trees, and which include the present variety of nectarine tree.

2. Classification of the Variety

The present variety of nectarine tree is embraced by Class 41, Plants, of the U.S. Patent Office Manual of Classification.

3. Prior Varieties

Among existing varieties of nectarine trees which are known to me, and mentioned herein, are the Summer Grand (U.S. Plant Pat. No. 2,879), Sun Grand (U.S. Plant Pat. No. 974), and Flavortop (unpatented).

ORIGIN OF THE VARIETY

The present variety of nectarine tree was originated by me as an open pollinated seedling of the Summer Grand nectarine. A number of such seedlings were grown to fruition, in the aforesaid experimental orchard, under careful and continuing observation by me; the present variety being a selection from such seedlings which evidenced commercial promise.

ASEXUAL REPRODUCTION OF THE VARIETY

Asexual reproduction of the variety was successfully accomplished, under my direction and in the aforesaid experimental orchard, by budding; such asexual reproductions, in maturity, having run true to the original tree in all respects.

SUMMARY OF THE VARIETY

The present variety of nectarine tree is — characteristically — medium in size and vigor, upright-spreading, dense, and round-topped; foliated with medium size, ovate, lanceolate, acutely pointed leaves having a crenate margin, and opposite-irregular, medium size, green, uniform glands; flowers from plump, appressed, pubescent buds of medium size and length; the flowers, of medium season, being large and pink; and is a regular and productive bearer of large, firm-fleshed, visually attractive, globose, freestone fruit, uniform in size and shape, having yellow skin substantially overspread and blushed with red, and yellow flesh.

The present variety of nectarine tree is further characterized, in comparison with the Summer Grand, by freestone fruit having general resemblance but ripens about a week earlier, and substantially with the Sun Grand and Flavortop.

The present variety of nectarine tree is still further characterized, in comparison with the Summer Grand, by freestone fruit having a slightly more depressed apex and a generally broader base, and surface speckling — frequently present on Summer Grand fruit — rarely occurs.

The present variety of nectarine tree is further characterized, in comparison with the Sun Grand, by fruit which is larger and more highly colored.

The present variety of nectarine tree is further characterized, in comparison with the Flavortop, by freestone fruit which is more highly colored and substantially lacks surface speckling, and by a more depressed apex.

BRIEF DESCRIPTION OF THE DRAWING

The drawing is an illustration, by photographic reproduction in color, of a twig with leaves, and separate fruit; one of the latter being cut in half to expose the flesh and stone; the stone remaining in place in one of the halves.

DESCRIPTION OF THE VARIETY

The botanical details of this new and distinct variety of nectarine tree — with color definitions (except those in common color terms) referenced to Plochere Color System (in book form) — are as follows:

Tree:

*Size.*—Medium.

*Vigor.*—Medium.

*Growth.*—Upright-spreading.

*Density.*—Dense.

*Form.*—Round-topped.

*Production.*—Productive.

*Bearing.*—Regular bearer.

Trunk:

*Size.*—Medium.

*Texture.*—Medium.

Branches:

*Size.*—Medium.

*Texture.*—Medium.

*Color.*—New wood: green. Dull. Mature wood: brown.

Leaves:

*Size.*—Medium. Average length — 16.1 cm. Average width — 4.2 cm.

*Form.*—Ovate. Lanceolate. Acutely pointed.

*Thickness.*—Medium.

*Color.*—Medium green.

*Texture.*—Smooth.

*Margin.*—Crenate.

*Petiole.*—Medium length. Medium thickness.

*Glands.*—Average number — 3. Opposite — irregular. Medium size. Reniform. Green. Positioned on petiole near base of blade, and on the latter.

*Stipules.*—Shed as leaves mature.

Flower buds:

*Size.*—Medium.

*Length.*—Medium.

*Form.*—Plump. Appressed. Pubescent.

Flowers:

*Date of full bloom.*—Mar. 9th, 1980. Medium, as compared with other varieties.

*Size.*—Large.

*Color.*—Pink.

Fruit:

*Maturity when described.*—Firm ripe — July 14th, 1980.

*Date of first picking.*—July 11th, 1980.

*Date of last picking.*—July 22nd, 1980.

*Size.*—Uniform. Large. Average diameter axially — 69 mm. Average transversely in suture plane — 66 mm.

*Form.*—Uniform. Symmetrical. Globose.

*Suture.*—A shallow inconspicuous line extending from base to beyond, but discontinues at apex, with slight depression beyond pistil point.

*Ventral surface.*—Rounded slightly. Lipped toward apex.

*Lips.*—Nearly equal.

*Cavity.*—Rounded. Circular. Average depth — 10 mm. Average breadth — 18 mm.

*Base.*—Rounded.

*Apex.*—Rounded.

*Pistil point.*—Apical.

Skin:

*Thickness.*—Medium.

*Texture.*—Medium.

*Tenacity.*—Tenacious to flesh.

*Tendency to crack.*—None in wet-dry season.

*Color.*—Ground color — yellow. Blush color — red (Plate 17 — No. 385 — Crimson Glory).

*Down.*—Wanting.

Flesh:

*Color.*—Yellow (Plate 9 — No. 195 — Clivia) streaked with red. Surface of pit cavity: red with pink fibers.

*Amygdalin.*—Wanting.

*Juice.*—Moderate.

*Texture.*—Firm. Melting.

*Fibers.*—Few. Tender.

*Ripens.*—Evenly.

*Flavor.*—Acid. Delicate.

*Aroma.*—Distinct.

*Eating quality.*—Best.

Stone:

*Type.*—Free. Parts from flesh smoothly, but with slight adherence to flesh along both dorsal and ventral edges.

*Fibers.*—Short.

*Size.*—Medium. Average length — 39 mm. Average breadth — 24 mm. Average thickness — 18 mm.

*Form.*—Obovoid.

*Base.*—Straight.

*Hilum.*—Oval.

*Apex.*—Rounded. Acuminate.

*Sides.*—Equal.

*Surface.*—Regularly furrowed toward apex. Ridged toward apex. Pitted from base to above center.

*Ridges.*—Rounded. Continuous.

*Pits.*—Elongated.

*Ventral edge.*—Thin, with wing throughout.

*Dorsal edge.*—Full, with shallow, broad groove throughout.

*Color.*—Brown (Plate 14 — No. 314 — Bronzio).

*Tendency to split.*—Slight in dry season.

Use: Market.

Keeping quality: Good.

Shipping quality: Good.

The nectarine tree and its fruit herein described may vary in slight detail due to climatic and soil conditions under which the variety may be grown; the present description being of the variety as grown in the Central Valley of California.

I claim:

1. A new and distinct variety of nectarine tree, substantially as illustrated and described, characterized, in particular, by freestone fruit having general resemblance to the Summer Grand but ripening about a week earlier, and ripening substantially with the Sun Grand and Flavortop.

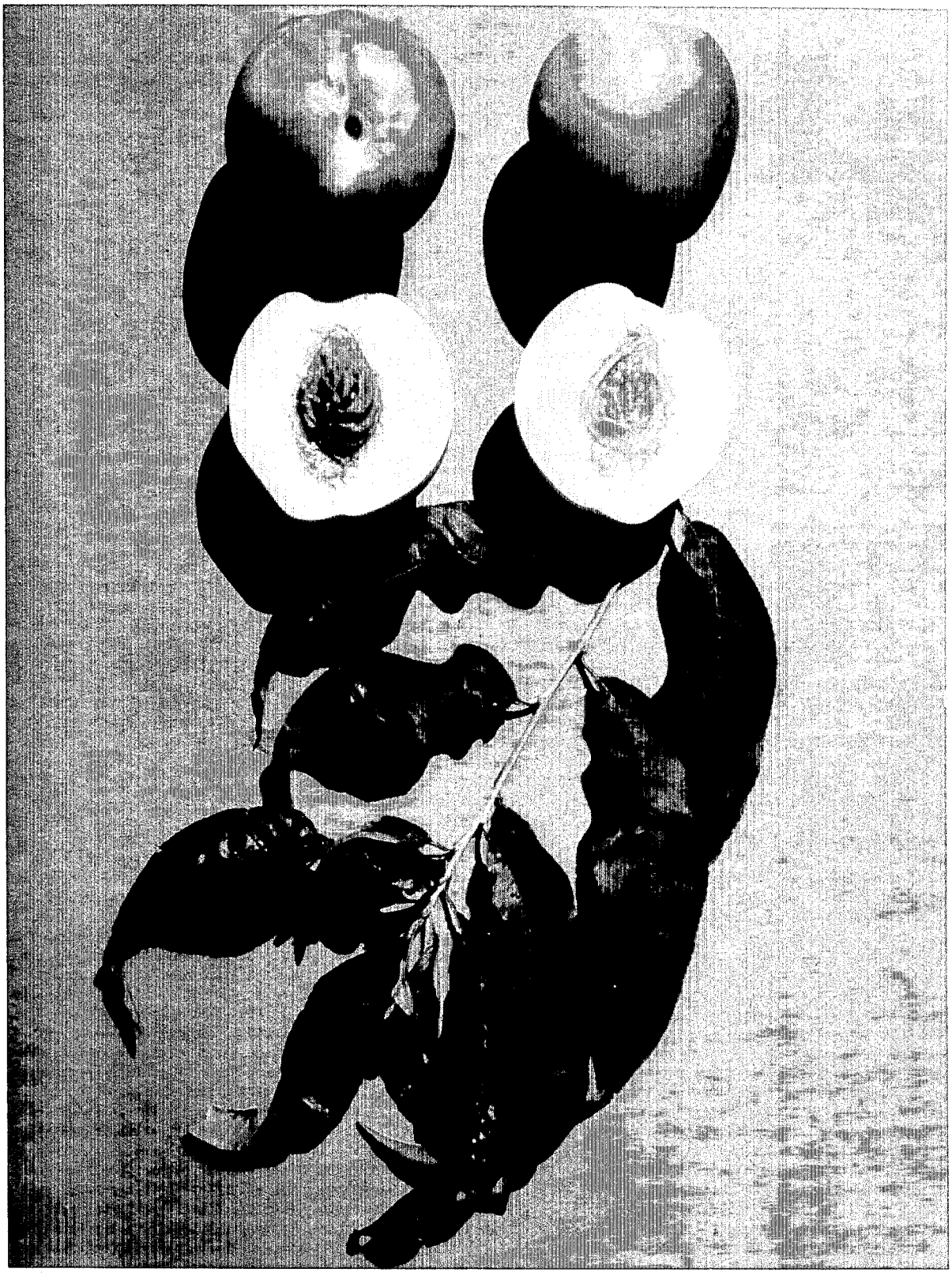

* * * * *